(12) United States Patent
Schirmer Almenara Ribeiro et al.

(10) Patent No.: US 11,372,009 B2
(45) Date of Patent: Jun. 28, 2022

(54) DIAGNOSTIC AND TREATMENT ASSEMBLY

(71) Applicant: Radiolife Co., Wilmington, DE (US)

(72) Inventors: Sergio Schirmer Almenara Ribeiro, Penn Valley, CA (US); Willians de Souza Dias, Sao Diogo I (BR)

(*) Notice: Subject to any disclaimer, the term of this patent is extended or adjusted under 35 U.S.C. 154(b) by 0 days.

(21) Appl. No.: 17/245,817

(22) Filed: Apr. 30, 2021

(65) Prior Publication Data

US 2021/0364537 A1 Nov. 25, 2021

Related U.S. Application Data

(63) Continuation-in-part of application No. 16/882,156, filed on May 22, 2020.

(51) Int. Cl.
   *G01N 22/00* (2006.01)
   *G01N 35/00* (2006.01)
   *B01L 3/00* (2006.01)

(52) U.S. Cl.
   CPC ........ *G01N 35/00732* (2013.01); *B01L 3/545* (2013.01); *G01N 22/00* (2013.01); *B01L 2300/022* (2013.01); *B01L 2300/024* (2013.01); *G01N 2035/00782* (2013.01); *G01N 2035/00851* (2013.01)

(58) Field of Classification Search
   None
   See application file for complete search history.

(56) References Cited

U.S. PATENT DOCUMENTS

| 2015/0035546 A1* | 2/2015 | Wang | G01N 15/1459 324/638 |
| 2015/0104783 A1* | 4/2015 | Al Ahmad | G01N 33/487 435/5 |

* cited by examiner

*Primary Examiner* — Paul S Hyun
(74) *Attorney, Agent, or Firm* — Stanton IP Law Firm, P.A.

(57) ABSTRACT

A diagnostic and treatment assembly, configured to diagnose and treat cellular disease. The diagnostic and treatment assembly has a radio wave generator communicatively coupled to a carrier modulator and a radio wave amplifier. An impedance matching system is electrically coupled to the radio wave amplifier. A reflected wave sensor is electrically coupled to the impedance matching system. A radiator applicator is electrically coupled to the reflected wave sensor. A vector impedance analyzer is electrically coupled to the radio wave amplifier. An information collector data network is electrically coupled to the vector impedance analyzer. A data logger is communicatively coupled to the carrier modulator, the vector impedance analyzer, and the reflected wave sensor. The diagnostic and treatment assembly operates in a low-power mode to diagnose a cellular disease and in a high-power mode to treat the cellular disease.

1 Claim, 14 Drawing Sheets

|   | 1 | 2 | 3 | 4 | 5 | 6 | 7 | 8 | 9 | 10 | 11 | 12 |
|---|---|---|---|---|---|---|---|---|---|----|----|----|
| A | 0,1056 | 0,1034 | 0,1115 | 0,107 | 0,1226 | 0,1048 | 0,1148 | 0,111 | 0,1116 | 0,1104 | 0,1062 | 0,1018 |
| B | 0,1078 | 0,1092 | 0,1109 | 0,1039 | 0,117 | 0,0984 | 0,103 | 0,1116 | 0,1126 | 0,1148 | 0,1069 | 0,1025 |
| C | 0,1128 | 0,1111 | 0,1159 | 0,1043 | 0,118 | 0,1058 | 0,1068 | 0,1055 | 0,115 | 0,1158 | 0,1177 | 0,1028 |
| D | 0,1244 | 0,1115 | 0,1142 | 0,1062 | 0,1182 | 0,1174 | 0,1061 | 0,1029 | 0,1013 | 0,1128 | 0,1142 | 0,1036 |
| E | 0,1147 | 0,1099 | 0,1136 | 0,1061 | 0,1153 | 0,1124 | 0,1027 | 0,1115 | 0,0975 | 0,1126 | 0,1134 | 0,1063 |
| F | 0,1146 | 0,1065 | 0,1153 | 0,1064 | 0,1142 | 0,115 | 0,0992 | 0,1022 | 0,1046 | 0,1114 | 0,1047 | 0,115 |
| G | 0,1146 | 0,1011 | 0,1087 | 0,1018 | 0,1033 | 0,113 | 0,1001 | 0,1081 | 0,1116 | 0,1119 | 0,1176 | 0,1124 |
| H | 0,1198 | 0,1033 | 0,1062 | 0,1083 | 0,1148 | 0,1075 | 0,1076 | 0,1115 | 0,105 | 0,1149 | 0,1241 | 0,1266 |

Fig. 6

| Power |   | LOW = 0.01W |   |   |   |   |   | MID = 0.1W |   | MAX > 1W |   |   |
|---|---|---|---|---|---|---|---|---|---|---|---|---|
|   | 1 | 2 | 3 | 4 | 5 | 6 | 7 | 8 | 9 | 10 | 11 | 12 |
| A | 0,1229 | 0,1086 | 0,1072 | 0,1138 | 0,1042 | 0,0879 | 0,0442 | 0,0491 | 0,0438 | 0,0442 | 0,0427 | 0,0446 |
| B | 0,1252 | 0,1148 | 0,1094 | 0,1 | 0,0963 | 0,087 | 0,0458 | 0,0406 | 0,0412 | 0,0487 | 0,0465 | 0,0433 |
| C | 0,1196 | 0,144 | 0,1087 | 0,1104 | 0,0959 | 0,0806 | 0,045 | 0,039 | 0,0403 | 0,0405 | 0,0393 | 0,0517 |
| D | 0,13 | 0,1198 | 0,1056 | 0,11 | 0,1018 | 0,0863 | 0,042 | 0,0398 | 0,0411 | 0,0439 | 0,0419 | 0,0458 |
| E | 0,1241 | 0,1176 | 0,1134 | 0,1033 | 0,0971 | 0,082 | 0,0426 | 0,0488 | 0,0436 | 0,0496 | 0,0416 | 0,0547 |
| F | 0,1212 | 0,1213 | 0,1106 | 0,1161 | 0,111 | 0,092 | 0,0508 | 0,0418 | 0,046 | 0,0534 | 0,0438 | 0,067 |
| G | 0,1221 | 0,1186 | 0,1161 | 0,1101 | 0,11 | 0,0898 | 0,0578 | 0,0503 | 0,0475 | 0,0495 | 0,0476 | 0,068 |
| H | 0,1266 | 0,1306 | 0,1155 | 0,1243 | 0,1218 | 0,1047 | 0,0589 | 0,0409 | 0,0541 | 0,0535 | 0,066 | 0,0715 |

DIAGNOSTIC AND TREATMENT ASSEMBLY

CROSS-REFERENCE TO RELATED APPLICATION

This application claims priority from U.S. patent application Ser. No. 16/882,156, filed May 22, 2020, titled DIAGNOSTIC AND TREATMENT ASSEMBLY which is hereby incorporated by reference herein for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

Trademarks used in the disclosure of the invention and the applicants make no claim to any trademarks referenced.

BACKGROUND OF THE INVENTION

1) Field of the Invention

The invention relates to the field of treatment and diagnostic medical devices, and, more particularly to a diagnostic medical device. More specifically, it relates to a detection and treatment instrument, and more particularly, to an instrument for detecting and treating cells using radio frequency waves.

Prior to embodiments of the disclosed invention, detecting and treating cellular illness without harming other healthy cells was extensively time consuming. Some other endeavors in this field include U.S. Pat. No. 9,320,911 issued to Szasz; U.S. Patent Application Pre-grant publication 2008/0319437 filed by Turner; and U.S. Patent Application Pre-grant publication 2008/0200803 filed by Kwon. Embodiments of the disclosed invention solve this problem.

2) Description of Related Art

Currently, the state of the art includes systems for detecting and treating cellular illness without harming other healthy cells was extensively time consuming.

In particular detecting and treating cellular illness without harming other healthy cells is difficult. For example, a mammography method is used to detect mammary cancer. However, the detection of mammary cancer using that method depends on the age of patients or structures of mammary tissues. It is easy to detect a problem in the mammary tissues using the mammary method, but it is dangerous to judge the abnormal lesion as cancer. Therefore, the same detection test should be repeated or other tests, such as ultrasonic diagnosis or biopsy, should be used.

Radiofrequency (RF) radiation, which includes radio waves and microwaves, is at the low-energy end of the electromagnetic spectrum. RF radiation has lower energy than some other types of non-ionizing radiation, like visible light and infrared, but it has higher energy than extremely low-frequency (ELF) radiation.

An example of the effectiveness of the use of radio frequency waves is when the radio waves are directed to cancer cells. Cancer cells have a size larger than a predetermined size and have a morphological variation. A biopsy can cause de-formation of cell shapes and has difficulty in judging metastasis of cancer cells. The above mentioned methods are the only methods currently used for detecting cancer, and thus an additional method for the detection and treatment of cancer should be considered.

However, the current devices do not provide a method to identify a disease state and treat the disease state.

Therefore, what is needed in the art is a device which can rapidly identify the disease state and can be optionally configured to treat the diseased cells if needed.

BRIEF SUMMARY OF THE INVENTION

The instant invention in one form is directed to increase longevity and reduce pain through technology and innovation. The technology of the instant invention is designed to help address some of the hardest problems faced by medicine which is a faster, cheaper, and more accurate diagnosis and treatment of diseases.

An advantage of the present invention is the ability to utilize the technology to diagnose diseases by detecting the presence of biological structures, like viruses, bacteria, and cancerous cells, and to treat diseases by inactivating such structures without harming healthy neighboring cells or biological structures.

A diagnostic and treatment assembly, configured to diagnose and treat cellular disease. The diagnostic and treatment assembly has a radio wave generator communicatively coupled to a carrier modulator and a radio wave amplifier. An impedance matching system is electrically coupled to the radio wave amplifier. A reflected wave sensor is electrically coupled to the impedance matching system. A radiator applicator is electrically coupled to the reflected wave sensor. A vector impedance analyzer is electrically coupled to the radio wave amplifier. An information collector data network is electrically coupled to the vector impedance analyzer. A data logger is communicatively coupled to the carrier modulator, the vector impedance analyzer, and the reflected wave sensor. The diagnostic and treatment assembly operates in a low-power mode to diagnose a cellular disease and in a high-power mode to treat the cellular disease.

In some embodiments, an electronic system is communicatively coupled to the data logger and is programmed with instructions to direct the radiator applicator to administer at least five but less than one hundred watts of power to a human in need of such diagnosis. The electronic system can be further programmed to analyze the relationship between energy sent and reflected to a body region under analysis with the data logger. The electronic system can be further programmed to measure phase and quadrature deviations between the wave originally generated by the equipment and the one that passed through the body under analysis with the data logger. The electronic system can be further programmed to determine cellular disease exists when the phase and quadrature deviations exceed ten percent.

In some embodiments, an electronic system is communicatively coupled to the data logger and is programmed with instructions to direct the radiator applicator to administer at least one hundred watts but less than one thousand watts of power to a human in need of such treatment.

BRIEF DESCRIPTION OF THE DRAWINGS

A further understanding of the nature and advantages of particular embodiments may be realized by reference to the remaining portions of the specification and the drawings, in which like reference numerals are used to refer to similar components. When reference is made to a reference numeral without specification to an existing sub-label, it is intended to refer to all such multiple similar components.

FIG. 6 shows a table showing the count of live cells per Elisa plate in the control sample;

FIG. 7 shows a table of the count of live cells per Elisa well in the sample containing cancer cells;

FIG. 8 is showing a table of the percentage of surviving cancer cells compared to control sample;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

Figure 1:
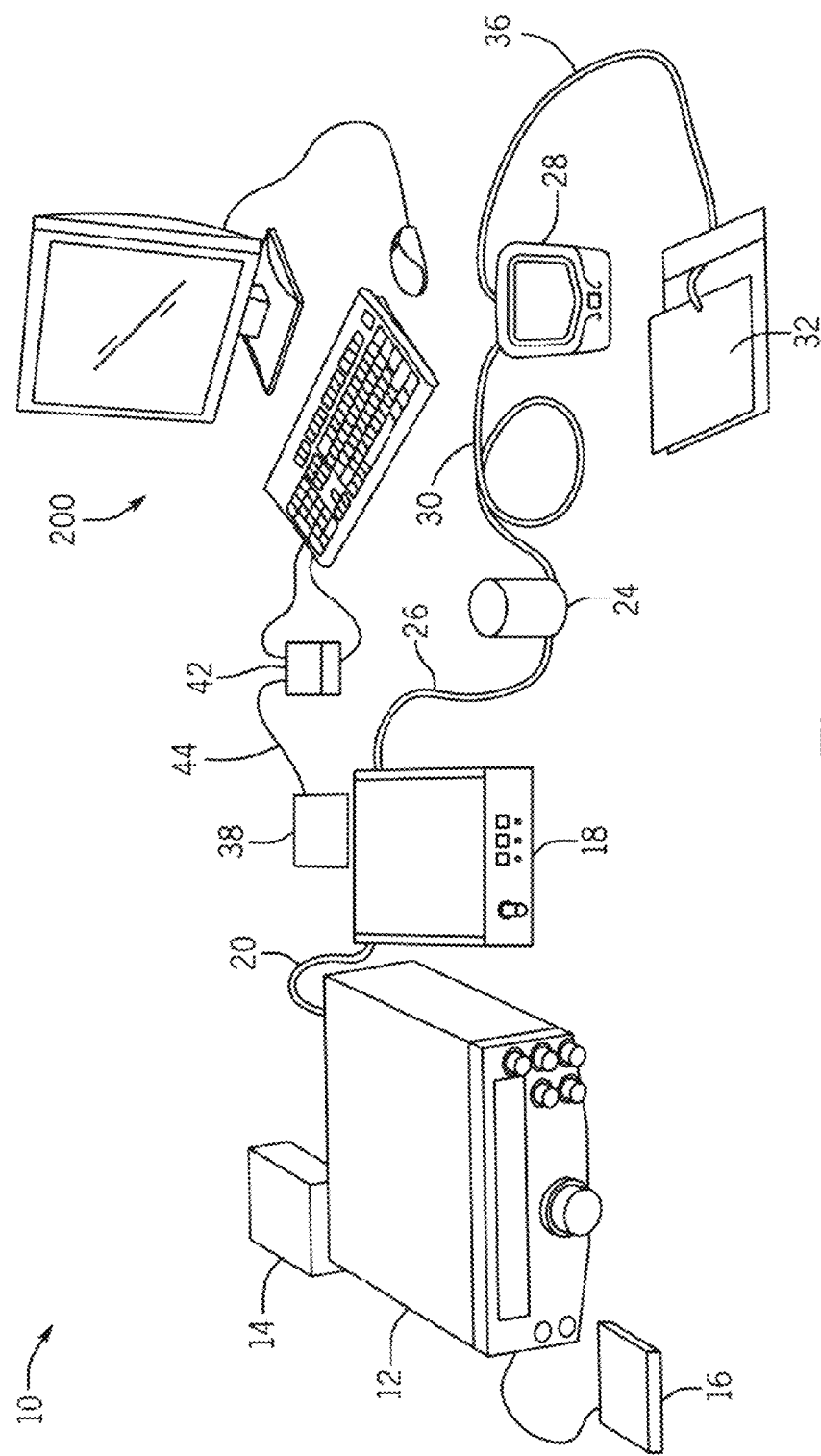
FIG. 1 shows a pictorial schematic diagram of one embodiment of the present invention.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

In this application the use of the singular includes the plural unless specifically stated otherwise and use of the terms "and" and "or" is equivalent to "and/or," also referred to as "non-exclusive or" unless otherwise indicated. Moreover, the use of the term "including," as well as other forms, such as "includes" and "included," should be considered non-exclusive. Also, terms such as "element" or "component" encompass both elements and components including one unit and elements and components that include more than one unit, unless specifically stated otherwise.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure be considered as an example of the principles of the invention and not intended to limit the invention to the specific embodiments shown and described.

The terms virus, cancer cell, cells are used interchangeably to mean cells that can be treated or diagnosed by the instant invention.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

The prior art does not provide for a system that is capable of diagnosing a condition or a viral infection using radio waves. The prior art includes U.S. Pat. No. 9,320,911, Issue Date: Apr. 26, 2016; U.S. Patent Application 20080319437, Publication Date: Dec. 25, 2008; and U.S. Patent Application 20080200803, Publication Date: Aug. 21, 2008 the contents of which are incorporated by reference in their entirety.

Figure 2:
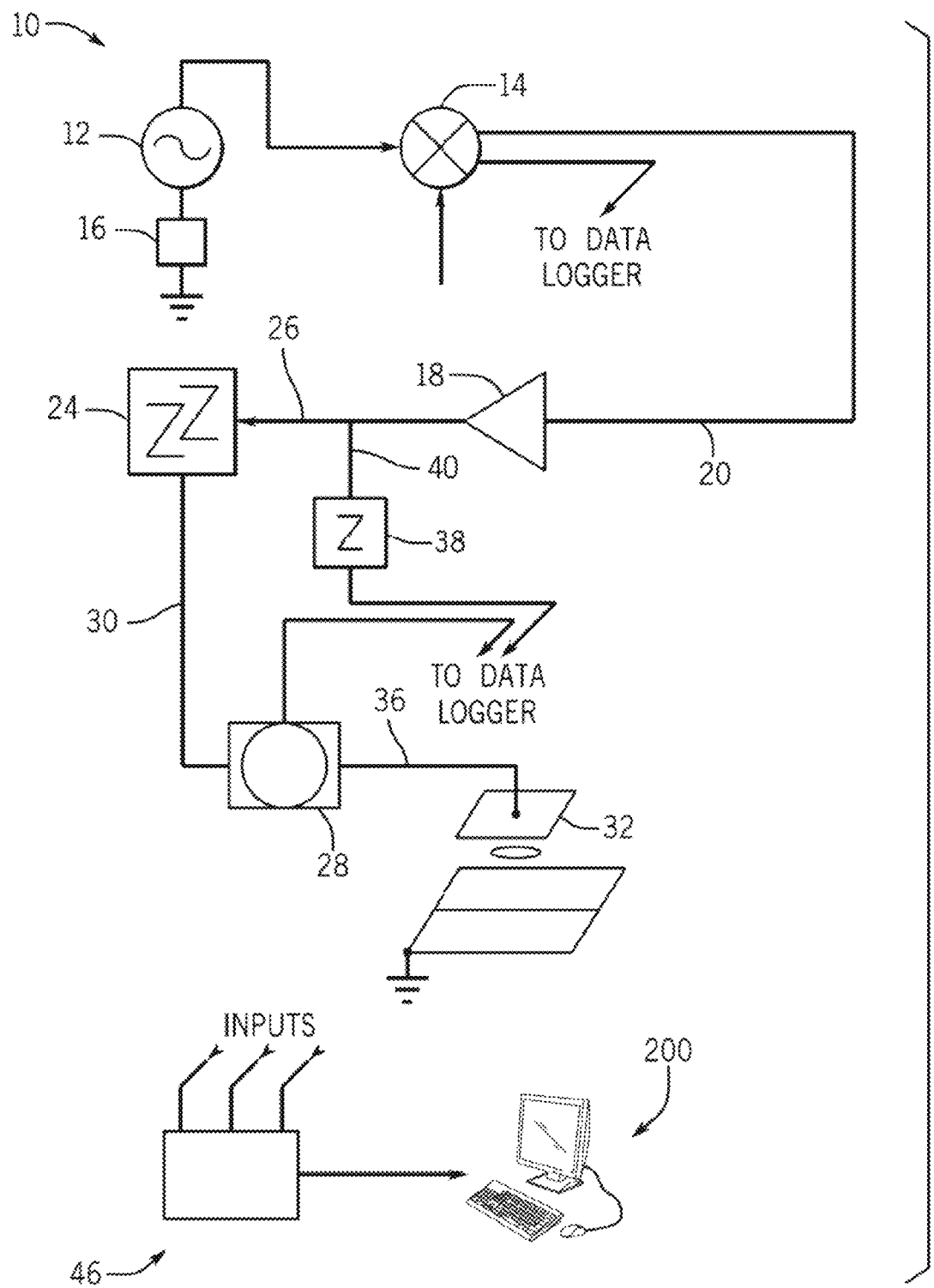
FIG. 2 shows a schematic of diagram of one embodiment of the present invention.

By way of example, and referring to FIGS. 1-2, one embodiment of a diagnostic and treatment assembly 10 further comprises a radio wave generator 12 communicatively coupled to a carrier modulator 14 and a metal bulkhead 16. The radio wave generator 12 is electrically coupled to a radio wave amplifier 18 with a first transmission line 20. An impedance matching system 24 is electrically coupled to the radio wave amplifier 18 with a second transmission line 26. A reflected wave sensor 28 is electrically coupled to the impedance matching system 24 with a third transmission line 30. A radiator applicator 32 is electrically coupled to the reflected wave sensor 28 with a fourth transmission line 36.

A vector impedance analyzer 38 is electrically coupled to the radio wave amplifier 18 with a fifth transmission line 40. An information collector data network 42 is electrically coupled to the vector impedance analyzer 38 with a sixth transmission line 44.

A data logger 46 is communicatively coupled to the carrier modulator 14, the vector impedance analyzer 38, and the reflected wave sensor 28. The data logger 46 is communicatively coupled to an electronic system 200.

Figure 3:
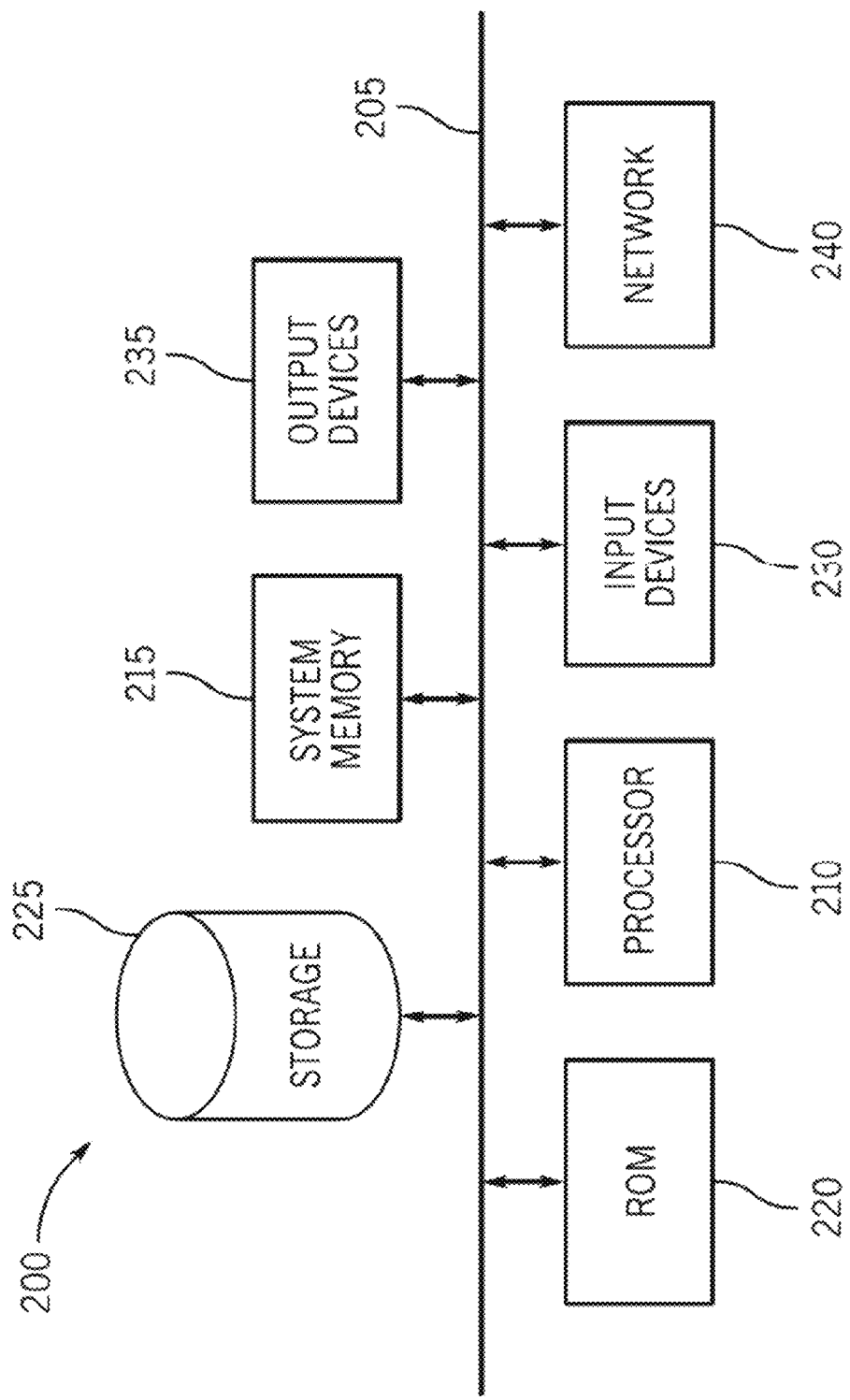
FIG. 3 shows a schematic of diagram of one embodiment of the present invention.

FIG. 3 conceptually illustrates the electronic system 200 with which some embodiments of the invention are implemented. The electronic system 200 may be a computer, phone, PDA, or any other sort of electronic device. An electronic system includes various types of computer readable media and interfaces for various other types of computer readable media. Electronic system 200 includes a bus 205, processing unit(s) 210, a system memory 215, a readonly-memory 220, a permanent storage device 225, input devices 230, output devices 235, and a network 240.

The bus 205 collectively represents all system, peripheral, and chipset buses that communicatively connect the numerous internal devices of the electronic system 200. For instance, the bus 205 communicatively connects the processing unit(s) 210 with the read-only-memory 220, the system memory 215, and the permanent storage device 225.

From these various memory units, the processing unit(s) 210 retrieves instructions to execute and data to process in order to execute the processes of the invention. The processing unit(s) may be a single processor or a multi-core processor in different embodiments.

The read-only-memory (ROM) 220 stores static data and instructions that are needed by the processing unit(s) 210 and other modules of the electronic system. The permanent storage device 225, on the other hand, is a read-and-write memory device. This device is a non-volatile memory unit that stores instructions and data even when the electronic system 200 is off. Some embodiments of the invention use a mass-storage device (such as a magnetic or optical disk and its' corresponding disk drive) as the permanent storage device 225.

Other embodiments use a removable storage device (such as a floppy disk or a flash drive) as the permanent storage device 225. Like the permanent storage device 225, the system memory 215 is a read-and-write memory device. However, unlike storage device 225, the system memory 215 is a volatile read-and-write memory, such as a random access memory. The system memory 215 stores some of the instructions and data that the processor needs at runtime.

In some embodiments, the invention's processes are stored in the system memory 215, the permanent storage device 225, and/or the read-only 220. For example, the various memory units include instructions for processing appearance alterations of displayable characters in accordance with some embodiments. From these various memory units, the processing unit(s) 210 retrieves instructions to execute and data to process in order to execute the processes of some embodiments.

The bus 205 also connects to the input and output devices 230 and 235. The input devices enable the person to communicate information and select commands to the electronic system. The input devices 230 include alphanumeric keyboards and pointing devices (also called "cursor control devices"). The output devices 235 display images generated by the electronic system 200. The output devices 235 include printers and display devices, such as cathode ray tubes (CRT) or liquid crystal displays (LCD). Some embodiments include devices such as a touchscreen that functions as both input and output devices.

Finally, as shown in FIG. 3, bus 205 also couples electronic system 200 to a network 240 through a network adapter (not shown). In this manner, the computer can be part of a network of computers (such as a local area network ("LAN"), a wide area network ("WAN"), or an intranet), or a network of networks (such as the Internet). Any or all components of electronic system 200 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more sets of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The diagnostic and treatment assembly 10 has a diagnostic mode of operation and a treatment mode of operation.

The diagnostic mode generally lasts no longer than one hour. During this time, the radiator applicator 32 generates wave power of at least 5 watts but no more than 100 W. Then, the data logger 46 analyzes the relationship between energy sent and reflected to the body region under analysis. After that, the data logger 46 measures phase and quadrature deviations between the wave originally generated by the equipment and the one that passed through the body under analysis. Finally, if the deviations are greater than 10%, the electronic system 200 indicates cell disease, such as cancer, due to the resonance with the specific cell density. The location of the cell disease is called a treatment area.

In the treatment mode, the radiator applicator generates wave power of at least 100 watts but no more than 1000 watts directed to the treatment area. In the presence of this wave, the Krebs cycle of diseased cells is interrupted, which, after a period of several hours, leads to death of the diseased cells.

As described, the instant invention is a device that uses a method to differentiate and detect biological nanostructures and to treat biological diseases. The instant invention is based on the induction of high frequency magnetic resonance in the sample, in the ultrahigh frequency (UHF) and super high frequency (SHF) bands. This process generates two pieces of information for each frequency the sample is exposed to:

The sample absorption rate; and

The phase difference between the signal transmitted and received, in order to measure the magnetic reluctance.

Figure 4:
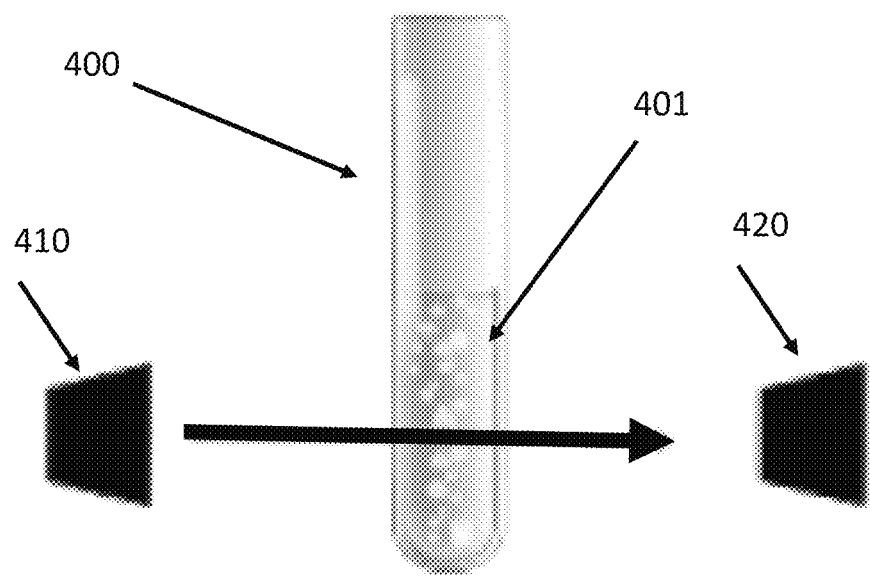
FIG. 4 is a simple depiction of the sample and the transmitter and receiver of the instant invention.

Referring to FIG. 4 which shows a simplified drawing of the instant invention you can see a test tube 400 with a biological sample 401 in it, as well as a transmitter 410 and a receiver 420. The sample 401 is crossed by radio waves generated by the transmitter 410 and the receiver 420 will capture the energy that has not been absorbed by the sample 401. The difference between the energy transmitted and the energy received results in the energy absorbed by the sample 401.

Once the absorption for a frequency range in a variable magnetic field is detected, the alignment times (at the moment of transmission) and misalignment of the dipoles (moment when the transmission of the Radio Frequency (R.F.) signal is interrupted) are verified. The difference between the alignment times result in the phase of the signal that crossed the sample. These time intervals, associated with the overall energy absorption of the sample, are tested at various frequencies in the UHF and SHF range, generating a spectral profile of what is contained in the sample. Knowing that each sample, solution, or material has a unique spectral profile signature, the technology is capable of differentiating these various signatures.

Figure 11:
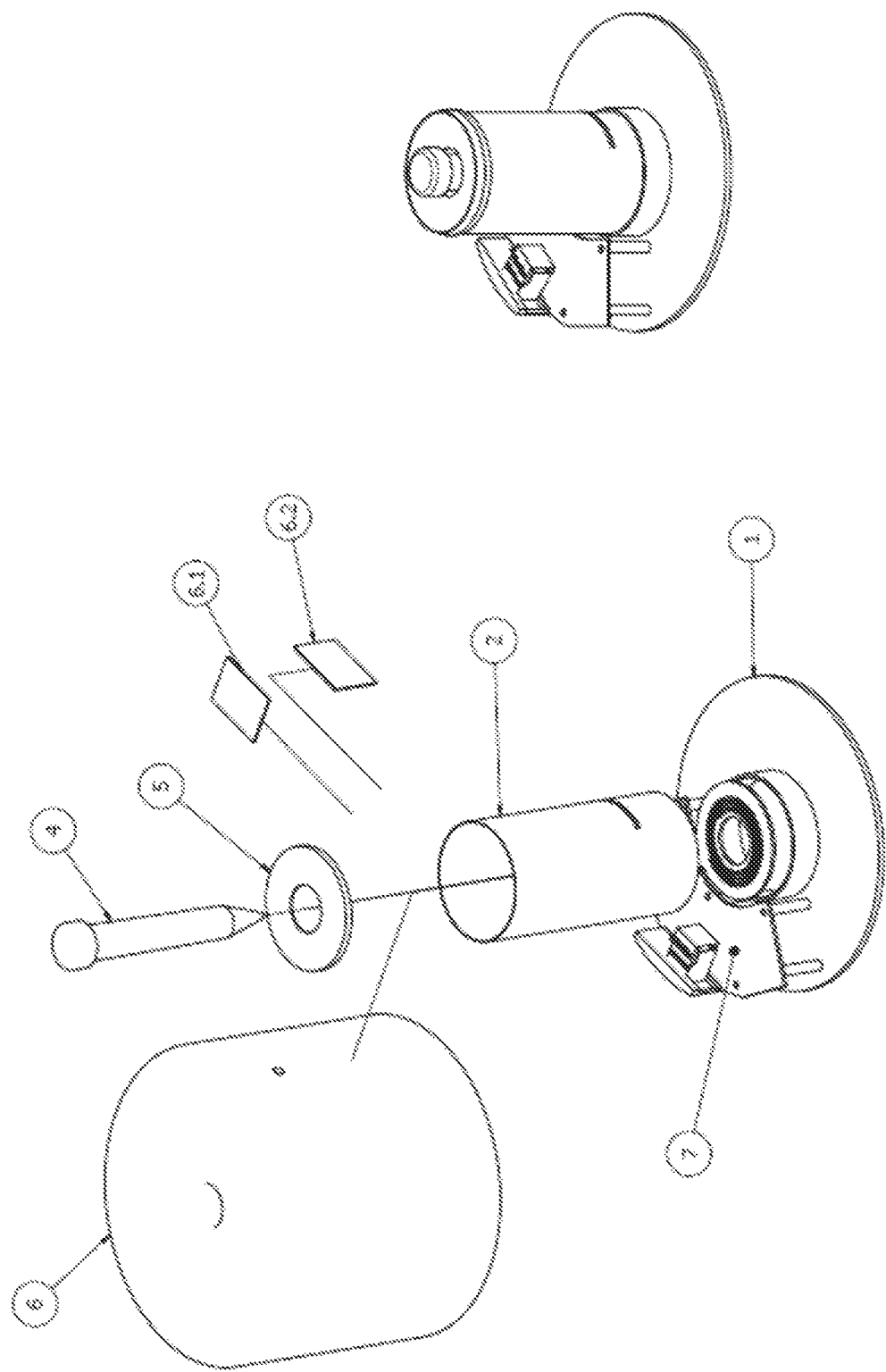
FIG. 11 shows an exploded view of the instant invention.

The instant invention measures the absorption of the sample 401. When in the presence of a variable electromagnetic field, the sample assumes alternating behaviors of magnetization and demagnetization states. At the time of magnetization, a component part of the circuit, which is item 16 of the components list related to FIG. 11 is responsible for reading how much energy has been absorbed by the sample.

The instant invention then measures the phase of the signal that crosses the sample.

When the field ceases, the sample is demagnetized and its magnetic dipoles misalign. At that moment, a voltage is generated by this demagnetization and is picked up by the antenna receiver and interpreted by the component item 16 of the components list related to FIG. 11. This device measures the phase, which is the time of misalignment of the particles until the end of the demagnetization.

The instant invention then measures the magnetic reluctance also known as reluctance, magnetic resistance, or a magnetic insulator which is defined as the opposition offered by a magnetic circuit to the production of magnetic flux.

The instant invention then measures the range of frequencies also known as the spectrum of the sample. The instant invention needs to understand the size of the structures which are being analyzed so that the instant invention knows the frequency that the structure resonates with.

Once you know the size of the structure the instant invention is able to calculate the fundamental frequency to resonate with the structure.

To determine the size and frequency required research to find the sizes of the structures that are relevant to our determining diagnostic signatures for carious disseated cells. The research created the following data:
  a. Virus—200 to 500 nm—"Virus frequencies have been measured for many years by engineer André Simoneton and it shows that all viruses vibrate at low frequencies, below 5000 angstroms (1 angstrom=0.0001 μm)."
  b. BCL-2 Proteins (Relevant for cancer detection and treatment)—3 to 6 nm—"A simple rule of thumb for thinking about typical soluble proteins like the Rubisco monomer is that they are 3-6 nm in diameter."
  c. Mitochondria (Relevant for cancer detection and treatment)—0.5 to 1 μm—"Mitochondria are organelles typically ranging in size from 0.5 micrometer to 1 micrometer in length, found in the cytoplasm of eukaryotic cells."
  d. Bacteria—0.2 to 2 μm—"In general, bacteria are between 0.2 and 2.0 μm—the average size of most bacteria."

Knowing the sizes of the structures one can see that the smallest structure is the virus, around 200 nm as opposed to the largest structure, around 2 μm. Therefore, this gives a range of frequencies from 1500 Terahertz (THz) to 150 THz.

The electronics capable of generating signals in the range of hundreds of THz is currently restricted in the laboratory environment and is still being studied. Therefore, to overcome this problem the invention uses a harmonic resonant of the fundamental frequencies. "Harmonics are the sinusoidal voltage or current that is an integer (whole number) at a multiple of the fundamental frequency at which the supply system is designed to operate."

Therefore, for each target to be to identify, one must calculate the harmonic range for that structure and set up the hardware to run a spectral analysis for the samples in the range calculated. As explained the spectral analysis will give two outputs for each frequency (absorption and phase). This data, complemented with the control sample test result serves as the input for the learning stage.

The Learning Stage of the development. When given a specific sample let's say a virus, the instant invention processes it and returns the values of absorption of frequency and electromagnetic phase regarding a predefined channel. Next the process is to evaluate a range of 250 different channel values in order to better discriminate the attributes. From these outputs, it is possible to assess which channel better separates the samples into positive and negative groups. The channel selection is performed as follows: the data is grouped by the diagnostics, then the system calculates the difference of absorption of frequency between both groups. The channel that presents the greatest difference (i.e., greatest separability between positives and negatives) for the sample (the virus) is selected. The overall process of this approach is illustrated in the FIG. 5 which illustrates the presence of the virus detection.

Subsequently, the instant invention builds a dataset containing the attributes regarding the best channel. From the dataset, the instant invention is able to employ a machine learning algorithm to induce a model that predicts the diagnostic of samples analyzed by the instant invention. More specifically, the instant invention has trained a random forest to accomplish it, although the instant invention has assessed different algorithms, such as logit, decision trees, support-vector machine (SVM), etc. This allows the instant invention to use a small amount of data.

The technology of the instant invention is a platform to improve the process of diagnosing and treating multiple diseases caused by viruses as but not limited to Influenza, Coronavirus, Sars-Cov-2, HIV, Herpes, Dengue, Zika, etc., bacteria such as but not limited to Strep throat, *E. Coli, Salmonella*, etc., or tumorous cells such as but not limited to breast cancer, skin cancer, lung cancer, prostate cancer, etc.

The process explained has been applied to the initial studies for human mammary tumorous cells and for Covid19, demonstrating that the same process can be applied to multiple diseases with results which are better or equal to the current Gold standard (PCR test—Polymerase chain reaction) currently used to identify the disease.

Turning the attention to the test for breast cancer. The methodology used by the instant invention for cancer diagnosis and treatment is developed on top of a modulated electro-hyperthermia methodology. This makes use of an already known principle for cancer treatment, modulated electro hyperthermia or mEHT. In short, it is about radiating radio waves in the 13 MHz band with high power causing heating of tumor cells—and other healthy cells around them—causing their death. Modulated electro-hyperthermia (mEHT) can induce an abscopal effect and thereby enhance the antitumor effects of immunotherapy.

The evaluation focused on understanding the phenomenon in order to counteract the side effects of the heating and death of healthy cells. Initially, in-vitro tests were performed on human mammary tumorous cells in order to determine the minimum potency per area that caused the effect and it was noticed that it was possible to cause the same effect (cell death) with a much lower power, which did not cause heating of the cells, by adding another frequency range, in the kilohertz (KHz) range, modulating the main wave of 13 Megahertz (MHz) in a single side band (pulsed wave).

The development of this technique used the same method of analysis explained previously where a wide test of modulations is applied.

The investigators noticed that the BCL-2 protein is an indication of the tumorous cells presence and its average size is 5 nm. That gives a fundamental frequency of 59 Petahertz (PHz). Calculating 'n'=4600000 they obtained 13 MHz as one of the harmonic frequencies of the BCL-2 fundamental frequency.

Since 13 MHz is the frequency used in traditional mEHT (with high powers and without selectivity), the researchers calculated the second harmonic at the top of the fundamental, resulting in a frequency of 2.8 KHz, allowing the use of low potencies and a high degree of selectivity for the diagnosis and treatment of cancer.

Modulated electro hyperthermia or mEHT innovation with pulsed waves for cancer treatment. As described, mEHT alone is not able to prevent damage to the healthy cells that are proximal to the cancer cells. The investigators undertook laboratory tests to determine a way to innovate the mEHT process by making it selective, affecting only cancer cells.

The first step was to experimentally determine the power limit at 13 MHz applied with the 2.8 KHz pulses that maximized the impact on cancer cells because this modulation is a harmonic of the BCL-2 protein. This protein is widely present in tumor cells of several cancers and the 2.8 KHz modulation was adopted in order to maximize the impact on tumor cells. The sample tumor cells were placed in Elisa plates. To maximize the impact on tumor cells, a test system containing a transmitter at the frequency of 13 MHz was modulated, modulating this wave at 2.8 KHz and a dipole antenna with a special arrangement to cause a power gradient in the wells of the Elisa plates. Setup containing transmitter, and Elisa plates inside the dipole antenna FIG. 13 and Elisa plates inside the antenna—the right side is the negative control sample FIG. 14.

The tests were performed using healthy human mammary cells (L929) for control and L929 with laboratory-induced cancer. The cells were always cultured together—to guarantee equivalence in their lifetime—and three replicates were cultured for a wide analysis, which would guarantee repeatability in the results.

After the tests with an irradiation duration of 3 hours each, it was noticed that the cancer cells had a much greater impact compared to the control sample. In the figure to the left, the formation of bubbles can be seen in the control samples FIG. 15 and in the cancerous samples in Elisa's plate FIG. 16.

After each irradiation, a cell survival count is performed, with the proper mapping of the minimum useful power that would cause the impact. This allowed comparison between the mEHT and modulated mEHT technologies.

FIG. 6 worksheet shows the amount of healthy L929 cells in each well of the Elisa plate that has the control samples. All the numbers are multiplied by $2.10 \times 10^4$.

FIG. 7 worksheet shows the amount of L929 cells with cancer in each well of the Elisa's plate. All the numbers are multiplied by $2.10 \times 10^4$.

Also, there are three regions:

1. The first one, called LOW=0.01 W, is the low power area (that received 0.01 W).

2. The second region, called MID=0.1 W, is the mid power area (that received 0.1 W).

3. The third one, called MAX>1 W, is the high power area (that received 1 W). This last power is considered the initial power to cancer treatments based on mEHT.

At the end of the tests, a considerable difference in the cancerous cell's death was observed in the areas of medium and high power. It was also found that using powers above the "MID POWER" zone did not add more results. Proving that low potencies, less than 1 W, kill just the cancerous cells, keeping the healthy cells alive because there is no heating.

The fact that it does not use high potencies (above 1 W) allows healthy cells to remain alive.

Figure 8:
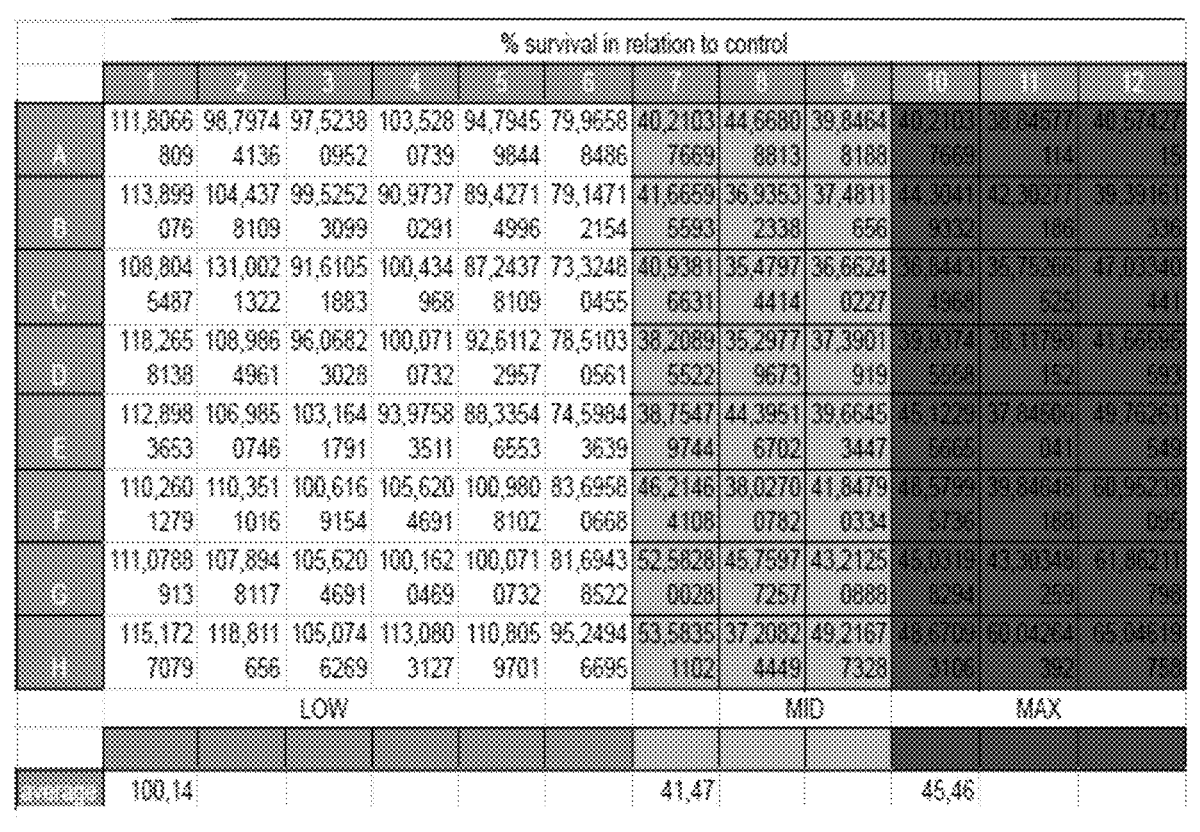

FIG. 8 worksheet shows the percentage of surviving cancer cells compared to control sample.

Once the set of modulations and frequencies that caused the cell death of the tumor cells, we experimentally investigated the cause of the death. We discovered that the tumor cells died by the Krebs cycle interruption. This interruption of the cycle was caused by the interaction of the chosen frequencies in the experiment with BCL-2 protein. This protein is directly related to the glucose flow to the inside of tumor cells. The explanation and details can be seen in the following reference Nature.com, Cell Research Published Dec. 8, 2017, Mitochondrial metabolism and cancer by Paolo Ettore Porporato, Nicoletta Filigheddu, José Manuel Bravo-San Pedro, Guido Kroemer and Lorenzo Galluzzi. https://www.nature.com/articles/cr2017155.

Therefore, it is clear that the instant invention has two modes of operation: diagnosis and treatment.

In the diagnostic mode, exactly the same technique is applied, where the instant invention observes the profile of the magnetic echoes caused by the magnetization and demagnetization of the analyzed sample to confirm the disease.

In the treatment mode, the irradiation duration is longer, in order to keep the tumorous cell's mitochondria out of operation long enough to cause its death of the cells.

The time required for cell death is monitored by the decay of magnetic echoes from tumor cells, making the dosage and duration of treatment ideal. It also serves to confirm the death of the target tumor.

Figure 9:
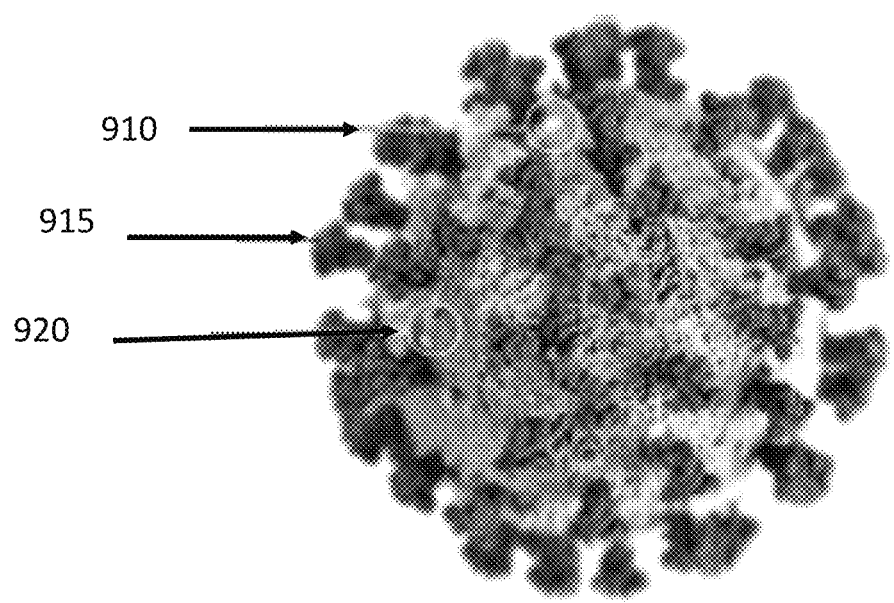
FIG. 9 is a model of the COVID-19 virus.

When the instant invention is used to detect a virus such as Covid 19 the instant invention resonates viral RNA by applying radio waves in the GHz range. Referring to FIG. 9, 910 is the E protein, 915 is the S protein and 920 is the M protein.

According to a study published in 2015 in the journal Nature, it is technically possible to resonate with viral RNA by applying radio waves in the GHz range. The Nature study experiences the fracture of the H3N2 and H1N1 viruses caused by the incidence of radio waves, causing the opposite displacement between the core and shell regions of the viral nanosphere, thus generating its disruption and inactivation of the virus.

Knowing that viruses are inert molecular structures, in general, with a size of around 500 nm, the resonance in the fundamental frequency of most viruses would be around 599 THz. In the special case of the Sars-Cov-2 Virus with a size in the range of 325.8 nm, the fundamental frequency of oscillation is approximately 920 THz.

As explained previously, the electronics capable of generating signals in the range of hundreds of THz is currently restricted in the laboratory environment and is still being studied. Thus, the investigators decided to use a harmonic resonant of the fundamental frequency of the Sars-Cov-2 virus with 'n'=500000. This gives us a central frequency of 1,850,000,000 Hz.

Laboratory tests were carried out and energy absorption was perceived in this frequency range. From this confirmation we started to analyze the magnetization and demagnetization times of the sample that resulted in small electrical echoes of energy. This result translates into a phase variation between the signal generated by the transmitter and the signal captured by the receiving antenna, as explained earlier.

The instant invention resulting from the research is a light and portable device developed for in-vitro analysis to detect among other diseases, the presence of the Sars-Cov-2 virus in saliva samples in a fast fashion (less than 10 seconds), dispensing the need for reagents. Because it does not use reagents, it can be rapidly deployed and at a low cost be used to test multiple samples which makes it ideal for mass testing programs.

The instant invention performs quick and precise tests in saliva samples to detect the Sars-Cov-2. The sample to be analyzed is crossed with radio waves at one of the harmonic frequencies that resonate with the virus structure. When it resonates, it absorbs energy and it is detected within a set of antennas especially calibrated to measure the energy emitted versus the energy absorbed. When there's a difference between both measurements, there's a positive detection for Covid19. This process, explained in more detail previously takes no more than 10 seconds.

The optimized device is shown in FIG. 10 and FIG. 11 provides an exploded view of the device.

The components that make up the system are shown in the tables below:

TABLE 1

| Item | Quantity | Part |
|---|---|---|
| 1 | 1 | Cylindrical base |
| 2 | 1 | Shielding tube |
| 4 | 1 | Falcon tube |
| 5 | 1 | Shielding lid |
| 6 | 1 | Top cover |
| 6.1 | 1 | Secondary board A, Metal sheet (touch sensor) |
| 6.2 | 1 | Secondary board B, Bluetooth, WIFI 802.11 b/g/n, Bluetooth v4.2 + EDR, Class 1, 2 and 3 Transceiver Module 2.4 GHz~2.5 GH - SURFACE MOUNT |
| 7 | 1 | Main board |

The Main Board is comprised of the following components:

TABLE 2

| Item | Quantity | Part |
|---|---|---|
| 1 | 1 | Battery holder CR2032 |
| 2 | 1 | BMT 1205XH9.5 |
| 3 | 1 | Ceramic Capacitors |
| 4 | 1 | Crystal 250 MHZ @30 PPM |
| 5 | 1 | ADS122CD41PWP |
| 7 | 2 | Diode array BAS40-04-7-F |
| 8 | 1 | Sensor AT42QT1010-TSHR |
| 9 | 1 | DC/DC Linear Regulator AP7361C-33SPR-13 |
| 10 | 1 | RTC Epson SOP14 COM Cristal |
| 11 | 1 | Bluetooth WIFI Module ESP32-WROOM-32D |
| 12 | 1 | Ethernet ControllerENC28J60-I/SO |
| 13 | 1 | Temperature and Moisture sensor S17021 |
| 14 | 1 | Intelligent Control LED WS2812-2020 |
| 15 | 1 | Watchdog Timer MAX6369KA |
| 16 | 1 | RF/IF gain and phase detector AD8302ARUZ |
| 17 | 1 | Flash Memory ATAES132A |
| 18 | 1 | RF LOW PASS FILTER M24C32-WMN6TP |
| 19 | 1 | RF LOW PASS FILTER DEA163800LT/LPF1608LL53R240A |
| 20 | 1 | CRYSTAL OSCILATOR TXETBDSANF |
| 21 | 1 | WIDE BAND SYNTHESIZER ADF4351BCPZ |
| 22 | 1 | RJ45 JACK JOO18D21E |
| 23 | 1 | INDUCTOR 1 uH |
| 24 | 7 | 1.5 Ohms @100 mhZ SIGNAL LINE FERRITE BEAD BLM18HE152SN1D |
| 25 | 1 | 251NDUCTOR 5.6 nH |
| 26 | 1 | 251NDUCTOR 15 nH |
| 27 | 1 | 251NDUCTOR 7.5 nH |
| 28 | 1 | LED YELLOW |
| 29 | 1 | Micro USB 10118192-0002If |
| 30 | 1 | LED RED |
| 31 | 17 | RESISTOR ¼ W 1% 2.32K |
| 32 | 1 | RF SHIELD BMI-S-103 |
| 33 | 1 | BALUN 1:1 - 5 TO 3000 MHz |
| 34 | 1 | USB RECEPTICAL, TYPE A |
| 35 | 1 | SMA CONNECTOR STR 50 OHM PCB |
| 36 | 1 | POWER AMPLIFIER HMC453ST89 |

In order to determine the sensitivity and specificity of the instant invention on diagnosing Covid19 from a saliva sample, the instant invention was used together with positive and negative control samples. These samples came from hospitals and point of care facilities located in the state of Espirito Santo, Brazil. As detailed in the trials flow below, those samples were inserted into the instant invention in order to collect the absorption and phase for each frequency in the wide spectrum of frequency from 1.4 GHz to 1.9 GHz. The first step is to collect and analyze a reference biological sample that does not have the virus or other pathogen or disease of interest. This becomes the standard for the testing of samples that are suspected of containing a virus or other pathogen or disease of interest. This reference sample can then be stored and used as a comparison in future test. As explained in more detail previously, after running more than 1000 samples, the data was processed and we were able to identify a high accuracy as explained below. The trial flow chart is shown in FIG. 12. The trial utilized 1357 samples and representative results are shown below.

| Sample | Standard | Instant invention |
|---|---|---|
| 1 | − | − |
| 2 | − | − |
| 3 | + | + |
| 4 | + | + |
| 5 | + | + |
| 6 | − | − |
| 7 | − | − |
| 8 | − | − |
| 9 | + | + |

-continued

| Sample | Standard | Instant invention |
|--------|----------|-------------------|
| 10 | − | − |
| 11 | − | − |
| 12 | − | − |
| 13 | − | − |
| 14 | − | − |
| 15 | − | − |
| 16 | − | − |
| 17 | + | + |

A plus symbol indicates positive result and a negative symbol indicates a negative result. The standard test was a PCR test (Polymerase chain reaction).

The results for the complete test can be found in the following table and in FIG. 17:

|  | Instant invention POSITIVE | Instant invention NEGATIVE | TOTAL |
|--|---|---|---|
| PCR Positive | 490 | 3 | 493 |
| PCR Negative | 0 | 864 | 864 |
| Total | 490 | 867 | 1357 |

The covid 19 test results resulted in a Sensitivity: Positive concordance rate: 490/493 (98.98%) Specificity: Negative concordance rate: 864/864 (100%) Total concordance rate: 1354/1357 (99.77%)

Referring now to the drawings, and more particularly to FIG. 4, it shows a simple depiction of the sample 401 in test tube 400 and the transmitter 410 and receiver 420 of the instant invention.

Figure 5:
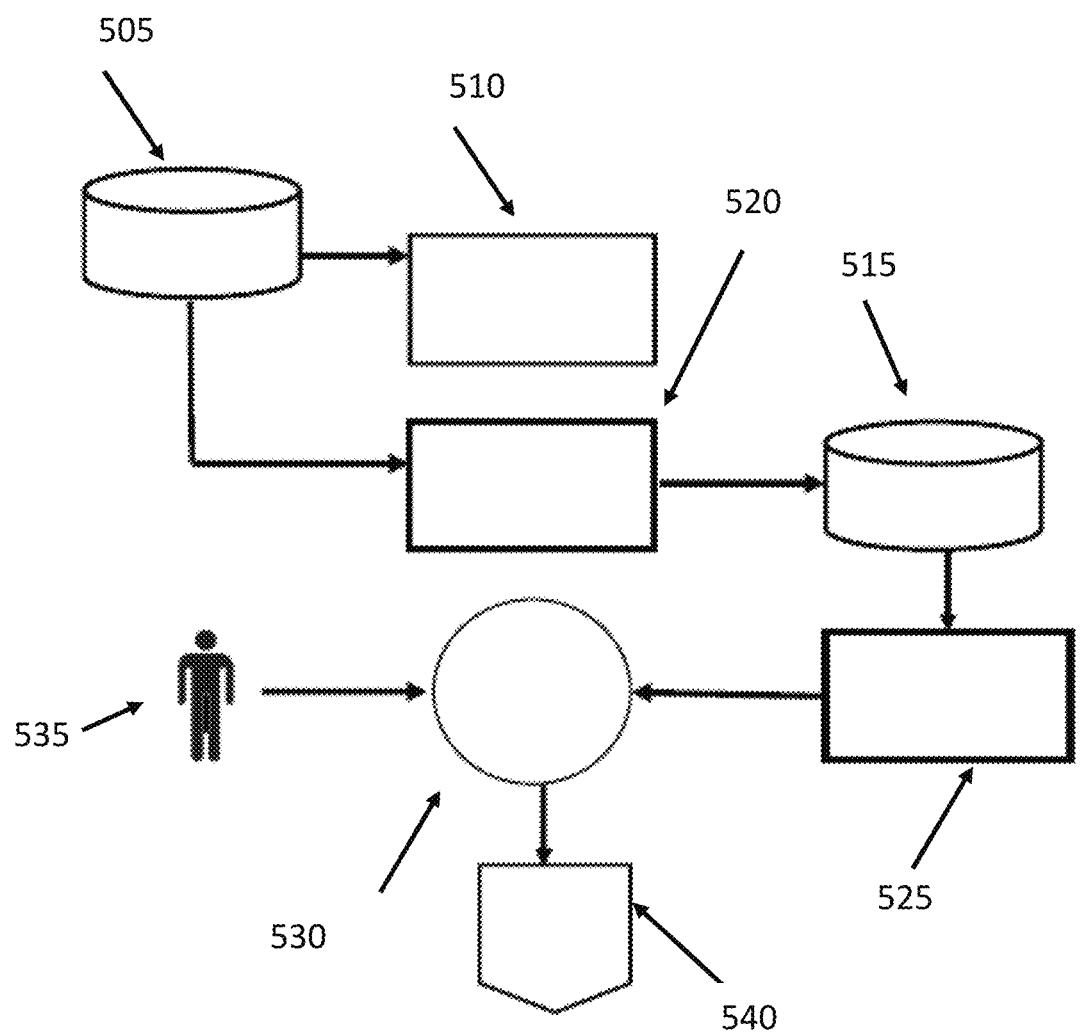
FIG. 5 is flow chart of algorithm to find the best channel.

FIG. 5 is a flow chart of algorithm to find the best channel. Raw data from the instant invention at step 505 is passed to step 510 finding the best channels and step 520 filtering raw data given the best channel which passes the data to step 515 subset from raw data. The system then uses a machine learning algorithm step 525 and compares it to the machine learning model 535. The operator then reviews the data and then it passes to diagnostic output step 540.

FIG. 6 shows a table showing the count of live cells per Elisa plate in the control sample.

FIG. 7 shows a table of the count of live cells per Elisa well in the sample containing cancer cells.

FIG. 8 is showing a table of the surviving cancer cells compared to control sample.

FIG. 9 is a model of the COVID-19 virus. Item 910 represents a typical E protein; item 915 represents a typical S protein; and item 920 represents a typical M protein.

Figure 10:
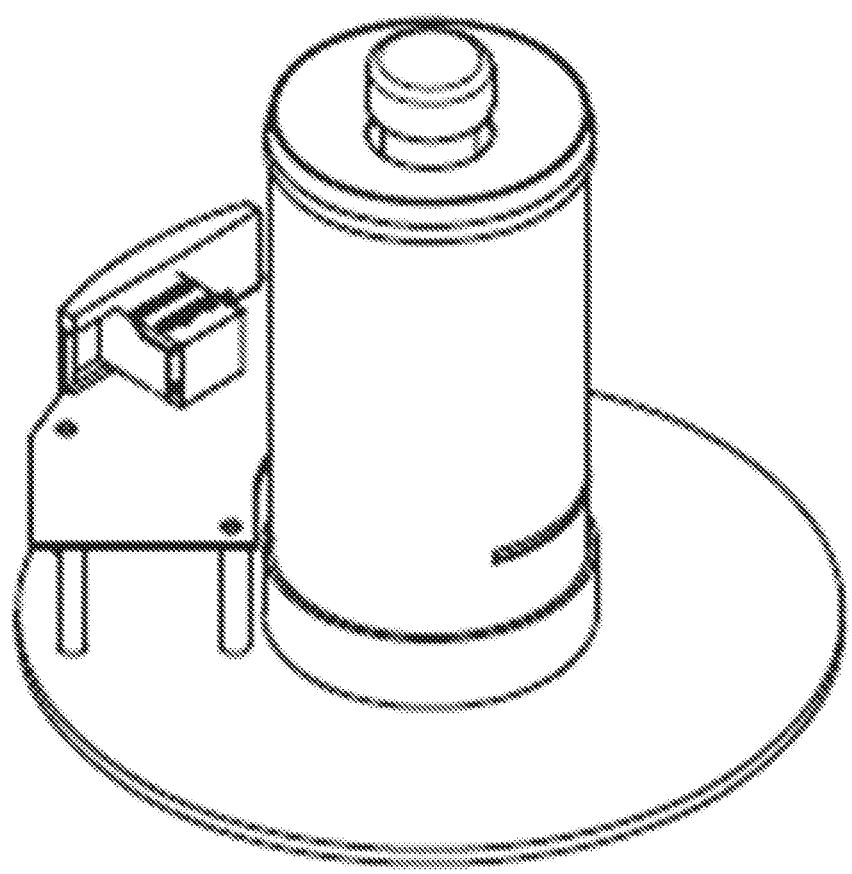
FIG. 10 shows the assembled view of the instant invention.

FIG. 10 shows the assembled view of the instant invention.

FIG. 11 shows an exploded view of the instant invention.

| Item | Quantity | Part |
|------|----------|------|
| 1 | 1 | Cylindrical base |
| 2 | 1 | Shielding tube |
| 4 | 1 | Falcon tube |
| 5 | 1 | Shielding lid |
| 6 | 1 | Top cover |
| 6.1 | 1 | Secondary board A, Metal sheet (touch sensor) |
| 6.2 | 1 | Secondary board B, Bluetooth, WIFI |
| | | 802.11 b/g/n, Bluetooth v4.2 + EDR, Class 1, 2 and 3 Transceiver Module 2.4 GHz~2.5 GH - SURFACE MOUNT |
| 7 | 1 | Main board |

Figure 12:
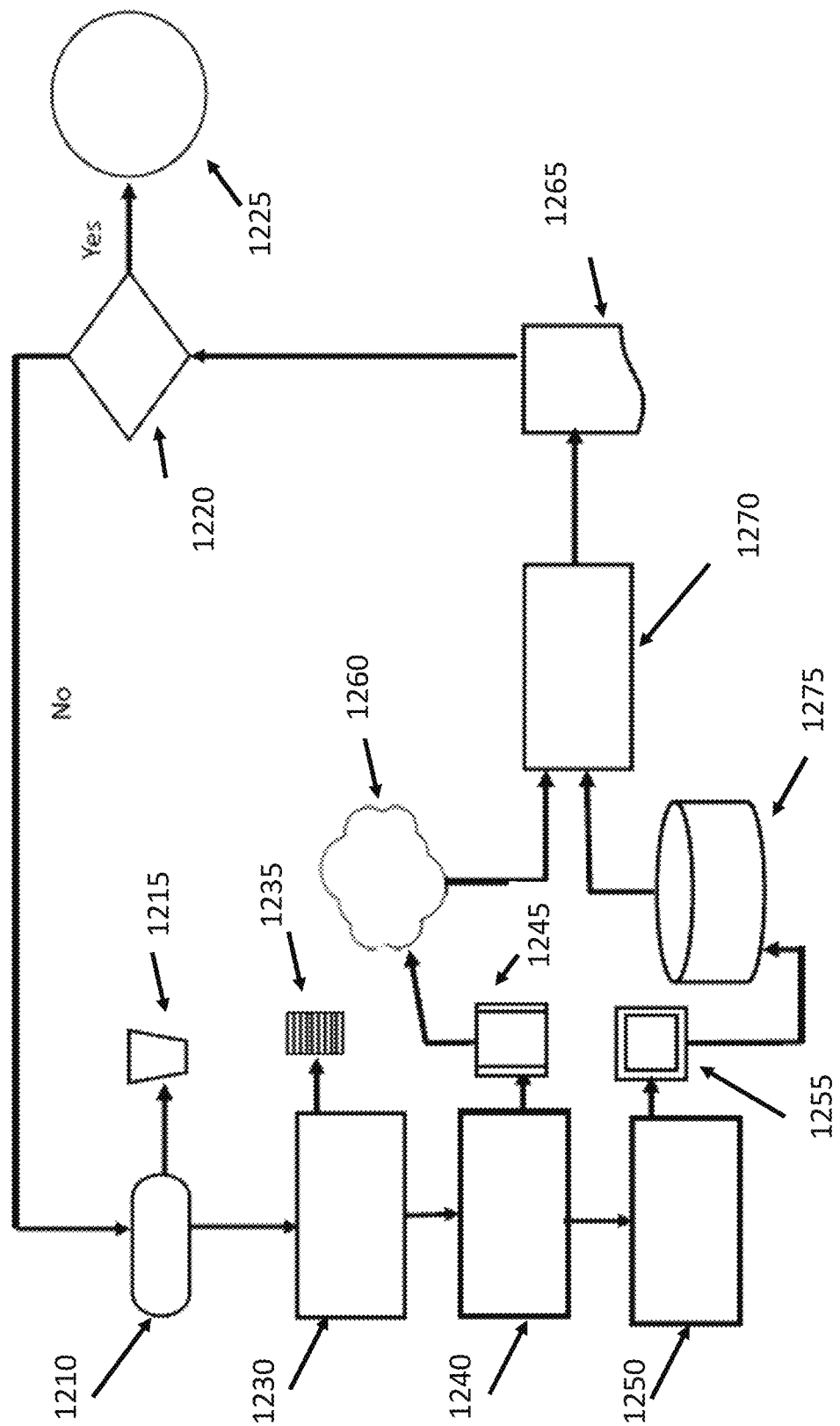
FIG. 12 shows a flow chart of the trial process.

FIG. 12 shows a flow chart of the trial process. Step 1210 is to collect the sample and place it is test tube 1215. Step 1230 is bar code reading and the bar code on test tube 1215 or another suitable container is read by barcode scanner 1235. The sample is processed in system 1240 and the system results 1245 are passed to the cloud 1260. The sample is then passed to the PCR testing apparatus 1250 and tested in PCR testing apparatus provides results 1255. Results 1255 are passed to the PCR database 1275. The PCR results 1255 are compared to the system results stored in the cloud 1260 at step 1270 and an analysis report is produced at step 1265. The report is reviewed by the lab personnel at step 1220 and the final report is released in step 1225. The process is continued until all the samples are processed.

Figure 13:
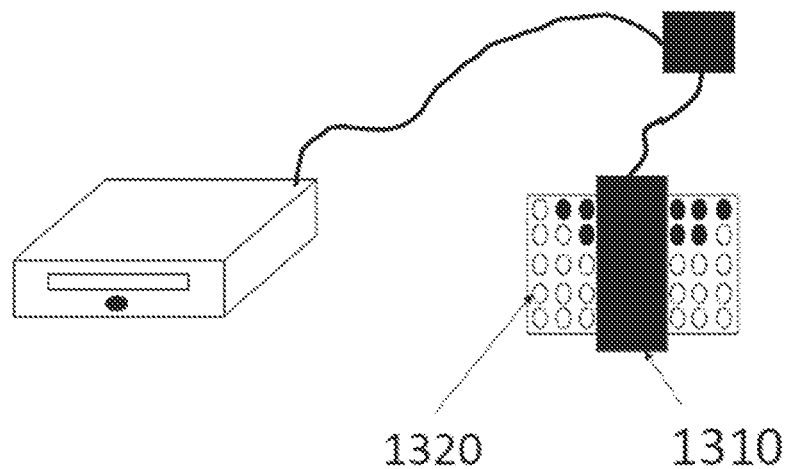
FIG. 13 shows a setup containing transmitter, and Elisa plates inside the dipole antenna.

FIG. 13 shows a setup containing antenna 1310 and Elisa plates 1320 inside the dipole antenna.

Figure 14:
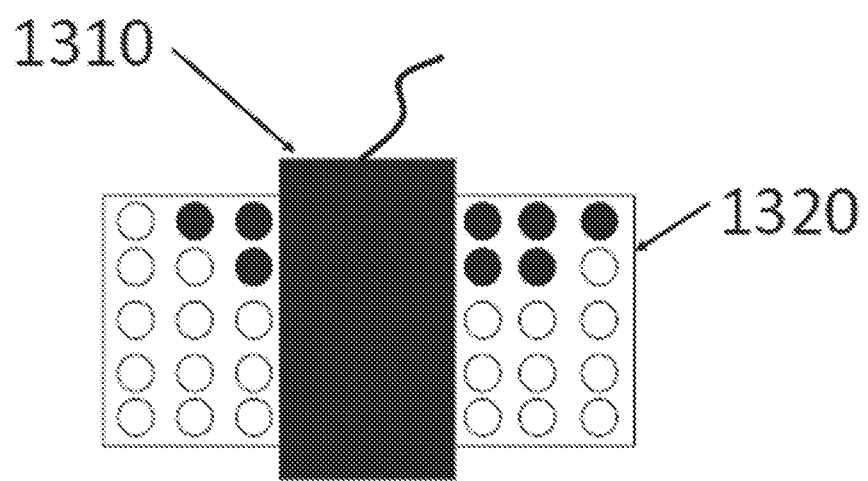
FIG. 14 shows an Elisa plate inside the antenna—the right side is the negative control sample.

FIG. 14 shows a close up view of an Elisa plate 1320 proximal to the antenna 1310 and Elisa plates 1320. The right side is the negative control sample.

Figure 15:
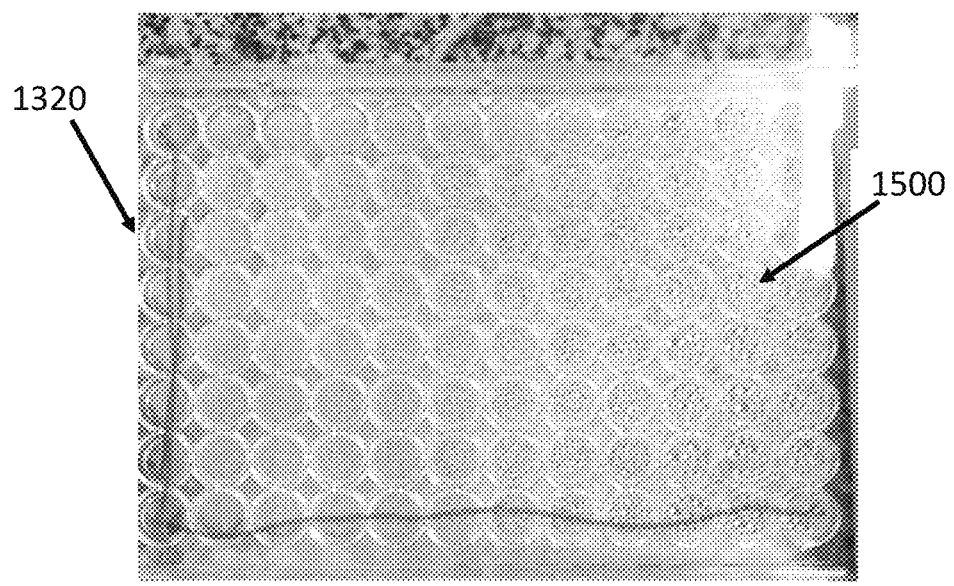
FIG. 15 shows an irradiation sample and the formation of bubbles in the control in Elisa's plate samples.

FIG. 15 shows an irradiation sample and the formation of bubbles 1500 in the control samples in Elisa's plate 1320.

Figure 16:
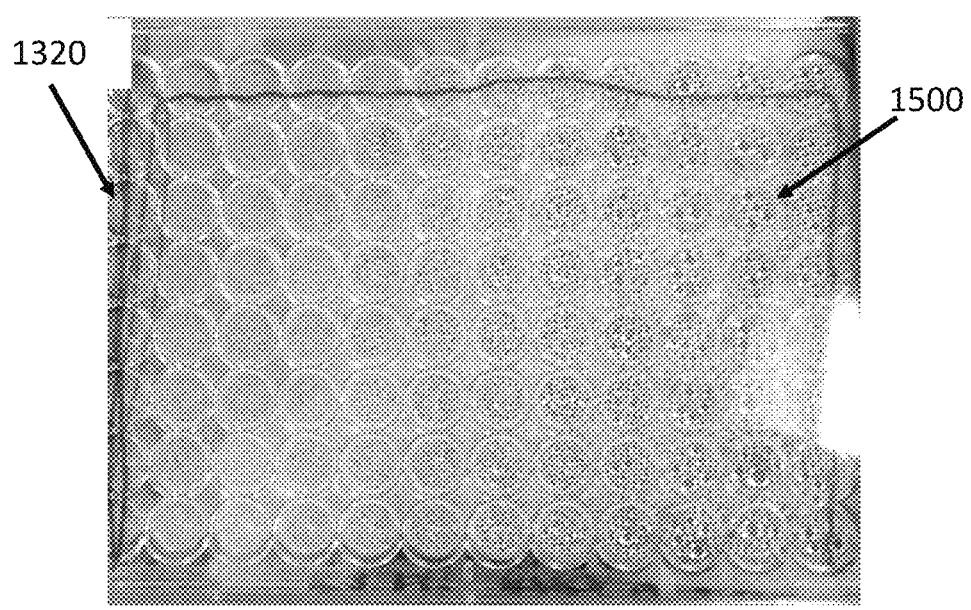
FIG. 16 shows an irradiation sample and the formation of bubbles in cancerous in Elisa's plate samples.

FIG. 16 shows an irradiation sample and the formation of bubbles 1500 in cancerous samples in Elisa's plate 1320.

Figure 17:
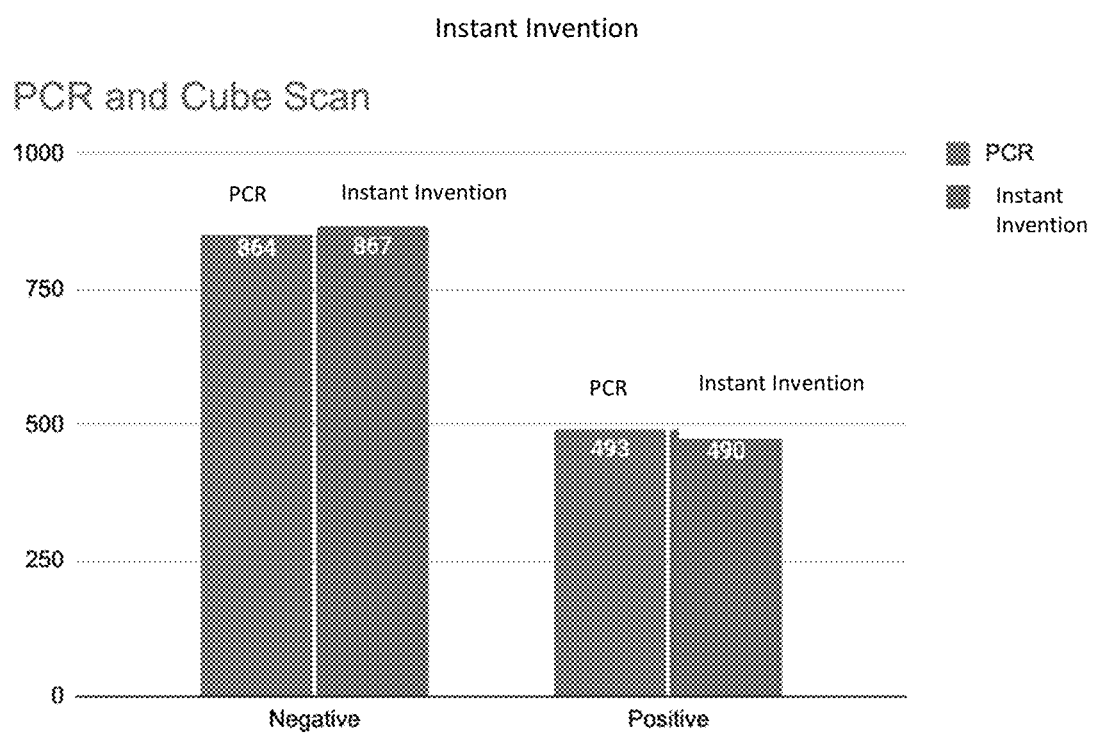
FIG. 17 shows results for the complete Covid-19 test.

FIG. 17 shows results for the complete Covid-19 test.

The system can be modified such that the energy absorption of the reference biological sample in a container is a stored value which is based on historical information.

In some embodiments, the system, method or methods described above may be executed or carried out by a computing system including a tangible computer-readable storage medium, also described herein as a storage machine, that holds machine-readable instructions executable by a logic machine such as a processor or programmable control device to provide, implement, perform, and/or enact the above described methods, processes and/or tasks. When such methods and processes are implemented, the state of the storage machine may be changed to hold different data. For example, the storage machine may include memory devices such as various hard disk drives, CD, flash drives, cloud storage, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, game controllers, video camera, camera, keyboard or gaming controller. For example, a user input may indicate a request that certain task is to be executed by the computing system, such as requesting the computing system to display any of the above described information, or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API).

Since many modifications, variations, and changes in detail can be made to the described embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

In addition, the present invention has been described with reference to embodiments, it should be noted and understood that various modifications and variations can be crafted by those skilled in the art without departing from the scope and spirit of the invention. Accordingly, the foregoing disclosure should be interpreted as illustrative only and is not to be interpreted in a limiting sense. Further it is intended that any other embodiments of the present invention that result from any changes in application or method of use or operation, method of manufacture, shape, size, or materials which are not specified within the detailed written description or illustrations contained herein are considered within the scope of the present invention.

Insofar as the description above and the accompanying drawings disclose any additional subject matter that is not within the scope of the claims below, the inventions are not dedicated to the public and the right to file one or more applications to claim such additional inventions is reserved.

Although very narrow claims are presented herein, it should be recognized that the scope of this invention is much broader than presented by the claim. It is intended that broader claims will be submitted in an application that claims the benefit of priority from this application.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of analyzing a suspected biological sample to determine the presence of SARS-Cov-2 virus comprising:
    a. collecting a reference biological sample that does not have the SARS-CoV-2 virus;
    b. collecting said suspected biological sample;
    c. placing said reference biological sample in a first test tube;
    d. placing said suspected biological sample in a second test tube;
    e. placing said first test tube in an analyzer and exposing said reference biological sample to a test frequency;
    f. said test frequency being 1.84 GHz;
    g. measuring said test frequency that has passed through said reference biological sample, and calculating a reference biological sample absorption rate and reference biological sample phase difference therefrom;
    h. generating a first spectral profile of said reference biological sample at said test frequency, said first spectral profile comprising said reference biological sample absorption rate and said reference biological sample phase difference;
    i. placing said second test tube in said analyzer and exposing said suspected biological sample to said test frequency;
    j. measuring said test frequency that has passed through said suspected biological sample, and calculating a suspected biological sample absorption rate and suspected biological sample phase difference therefrom;
    k. generating a second spectral profile of said suspected biological sample at said test frequency, said second spectral profile comprising said suspected biological sample absorption rate and said suspected biological sample phase difference; and
    l. comparing said first spectral profile to said second spectral profile, and if there is a difference, confirming a positive detection for said SARS-CoV-2 virus.

* * * * *